(12) United States Patent
Fattinger

(10) Patent No.: US 10,684,227 B2
(45) Date of Patent: **\*Jun. 16, 2020**

(54) METHOD FOR DETECTION OF BINDING AFFINITIES

(71) Applicant: Hoffmann-La Roche Inc., Nutley, NJ (US)

(72) Inventor: Christof Fattinger, Blauen (CH)

(73) Assignee: Hoffmann-La Roche Inc., Nutley, NJ (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/007,497

(22) Filed: Jun. 13, 2018

(65) Prior Publication Data

US 2018/0364174 A1 Dec. 20, 2018

Related U.S. Application Data

(63) Continuation of application No. 14/372,707, filed as application No. PCT/EP2013/050825 on Jan. 17, 2013, now Pat. No. 10,006,866.

(30) Foreign Application Priority Data

Jan. 17, 2012 (EP) ..................... 12151436

(51) Int. Cl.
*G01N 33/551* (2006.01)
*G01N 21/75* (2006.01)
(Continued)

(52) U.S. Cl.
CPC ........... *G01N 21/75* (2013.01); *G01N 21/552* (2013.01); *G01N 21/7743* (2013.01); *G01N 33/54373* (2013.01)

(58) Field of Classification Search
None
See application file for complete search history.

(56) References Cited

U.S. PATENT DOCUMENTS 4,647,544 A 3/1987 Nicoli et al.
6,395,558 B1 5/2002 Duveneck
(Continued)

FOREIGN PATENT DOCUMENTS

| CN | 1419658 A | 5/2003 |
|---|---|---|
| JP | H05-171732 | 7/1993 |
| JP | 2003-521728 | 7/2003 |

OTHER PUBLICATIONS

Capture Compound Mass Spectometry (CCMS), *Whitepaper*. 2010 pp. 1-6.

(Continued)

*Primary Examiner* — Christopher L Chin
(74) *Attorney, Agent, or Firm* — Mintz Levin Cohn Ferris Glovsky and Popeo, P.C.

(57) ABSTRACT

A method for the detection of binding affinities comprises providing a device having a planar waveguide (2) arranged on a substrate (3) and an optical coupler (4). Coherent light (1) of a predetermined wavelength is coupled into the planar waveguide (2) such that the coherent light propagates along the planar waveguide (2), with an evanescent field (6) of the coherent light propagating along an outer surface (5) of the planar waveguide (2). Target samples (8) attached to binding sites (7) are arranged along a plurality of predetermined lines (9) on the outer surface (5) of the planar waveguide (2). At a predetermined detection location, light of the evanescent field which is scattered by target samples (8) bound to binding sites (7) arranged along the predetermined lines (9) is detected. The light scattered by the target samples (8) bound to the binding sites (7) has, at the predetermined (Continued)

detection location, a difference in optical path length which is an integer multiple of the predetermined wavelength of the light.

20 Claims, 10 Drawing Sheets

(51) Int. Cl.
    *G01N 21/552*    (2014.01)
    *G01N 21/77*    (2006.01)
    *G01N 33/543*    (2006.01)

(56) References Cited

U.S. PATENT DOCUMENTS

| | | |
|---|---|---|
| 6,510,263 B1 | 1/2003 | Maisenholder et al. |
| 6,829,073 B1 | 12/2004 | Krol |
| 6,873,764 B2 | 3/2005 | Maisenholder et al. |
| 6,951,715 B2 | 10/2005 | Cunningham |
| 7,233,391 B2 | 6/2007 | Schermer |
| 9,405,069 B2 * | 8/2016 | Fattinger .......... G01N 33/54353 |
| 10,060,917 B2 * | 8/2018 | Fattinger ............ G01N 21/7743 |
| 10,156,524 B2 * | 12/2018 | Fattinger .......... G01N 33/54373 |
| 2003/0091284 A1 | 5/2003 | Maisenholder et al. |
| 2010/0053610 A1 | 3/2010 | Lee |
| 2015/0276612 A1 | 10/2015 | Fattinger |
| 2016/0139115 A1 | 5/2016 | Fattinger |
| 2016/0161477 A1 | 6/2016 | Fattinger |

OTHER PUBLICATIONS

Dulsner et al. "CCMS technology enables inproved proteomic analysis through functional isolation of subproteomes." Nature Publishing Group, 2008: an10-an11.

Koster et al. "Capture Compound Mass Spectrometry: A Technology for the Investigation of Small Molecule Protein Interactions." Assay and Drug Development Technologies. vol. 5 (2007) 381-391.

ZeptoREADER User Manual 2007.

Rogers et al. "Generating 90 nanometer features using near-field contact-mode photolithograph with an elastomeric phase mask." American Vacuum Society. (1998) pp. 59-68.

Stadler et al. Light-Induced In Situ Pattering of DNA-Tagged Biomolecules and Nanoparticles. IEEE Transactions on Nanobiocience vol. 5 No. 3 (2006) 215-219.

Ehrat et al. "Planar Waveguides: How Nano Layers Enable to Detect Zepto Moles of Macro Molecules in Pico Liter Spots on Micro Arrays." Workshop Photonic Sensors. (2009) pp. 1-15.

Aslan et al. "Plasmon Light Scattering in Biology and Medicine: New Sensing Approaches, Visions and Perspectives." Elsevier, Science Direct. (2008) pp. 538-544.

Sannomiya et al. "Single Plasmonic Nanoparticles for Biosensing." Elsevier LTD. Trends in Biology vol. 20 No. 7 (2011) pp. 343-351.

Pawlak et al. "Zeptosens' Protein Microarrays: A Novel High Performance Microarray Platform for Low Abundance protein Analysis." Proteomics (2002) 383-393.

International Search Report and Written Opinion Issued in PCT/EP2013/050825 dated Jul. 3, 2013.

English Abstract of JPH05-172732, entitled "method and Apparatus for Detecting Particle in Liquid" dated Jul. 9, 1993.

English Abstract of JP 2003-521728, entitled A Process for forming a lattice structure, optical element, evernescent field, optical coupler for communication technology, and wavelength monitoring device, dated Jul. 15, 2003.

English Abstract of CN 1419658 A, May 21, 2003, "Method for Producing a grid structure, and optical element, an evanescence field sensor plate, a microtiter plate and an optical communication engineering coupler".

* cited by examiner

METHOD FOR DETECTION OF BINDING AFFINITIES

CROSS REFERENCE TO RELATED APPLICATIONS

This disclosure is a continuation application of U.S. patent application Ser. No. 14/372,707 filed on Jul. 16, 2014, which is a 35 U.S.C. § 371 national stage entry of PCT/EP2013/050825, which has an international filing date of Jan. 17, 2013, which claims priority to European Patent Application No. 12151436.8 filed on Jan. 17, 2012. The disclosures of the patent applications referenced above are herein incorporated by reference in their entireties.

FIELD

The present invention relates to a device for use in the detection of binding affinities as well as a system and a method for the detection of binding affinities in accordance with the respective independent claim.

BACKGROUND

Such devices are used, for example, as biosensors in a large variety of applications. One particular application is the detection or monitoring of binding affinities or processes. For example, with the aid of such biosensors various assays detecting the binding of target samples to binding sites can be performed. Typically, large numbers of such assays are performed on a biosensor at spots which are arranged in a two-dimensional microarray on the surface of the biosensor. The use of microarrays provides a tool for the simultaneous detection of the binding affinities or processes of different target samples in high-throughput screenings, wherein large amounts of target samples like molecules, proteins or DNA can be analysed quickly. For detecting the affinities of target samples to bind to specific binding sites (e.g. the affinities of target molecules to bind to different capture molecules), a large number of binding sites is immobilised on the surface of the biosensor at spots which can be applied, for instance, by ink-jet spotting. Each spot forms an individual measurement zone for a predetermined type of capture molecules. The affinity of a target sample to a specific type of capture molecules is detected and is used to provide information on the binding affinity of the target sample.

A known technique for detecting binding affinities of target samples uses labels which are capable of emitting fluorescent light upon excitation. For example, fluorescent tags can be used as labels for labelling the target samples. Upon excitation, the fluorescent tags are caused to emit fluorescent light having a characteristic emission spectrum. The detection of this characteristic emission spectrum at a particular spot indicates that the labelled target molecule has bound to the particular type of binding sites present at the respective spot.

A sensor for detecting labelled target samples is described in the article "Zeptosens' protein microarrays: A novel high performance microarray platform for low abundance protein analysis", Proteomics 2002, 2, S. 383-393, Wiley-VCH Verlag GmbH, 69451 Weinheim, Germany. The sensor described there comprises a planar waveguide arranged on a substrate, and a grating for coupling coherent light of a predetermined wavelength into the planar waveguide. A further grating is arranged at that end of the planar waveguide remote from the grating for coupling the light into the waveguide. Coherent light that has propagated through the planar waveguide is coupled out of the waveguide by the further grating. The outcoupled light is used for adjustment of the coupling of coherent light of predetermined wavelength into the planar waveguide. The coherent light propagates through the planar waveguide under total reflection with an evanescent field of the coherent light propagating along the outer surface of the planar waveguide. The depth of penetration of the evanescent field into the medium of lower refractive index at the outer surface of the planar waveguide is in the order of magnitude of a fraction of the wavelength of the coherent light propagating through the planar waveguide. The evanescent field excites the fluorescent tags of the labelled target samples bound to the binding sites arranged on the surface of the planar waveguide. Due to the very small penetration of the evanescent field into the optically thinner medium at the outer surface of the planar waveguide, only the labelled samples bound to the binding sites immobilized on the outer surface of the planar waveguide are excited. The fluorescent light emitted by these tags is then detected with the aid of a CCD camera.

SUMMARY

While it is principally possible to detect the binding affinities using fluorescent labels, this technique is disadvantageous in that the detected signal is produced by the labels rather than by the binding partners themselves. In addition, labelling the target samples requires additional working steps. Moreover, labelled target samples are comparatively expensive. Another disadvantage is the falsification of the results caused by photobleaching or quenching effects.

It is an object of the present invention to provide a device for use in the detection of binding affinities of a target sample as well as a system and a method capable of detecting such binding affinities which overcome or at least greatly reduce the disadvantages of the prior art sensor described above.

In accordance with the invention, this object is achieved by a device for use in the detection of binding affinities. The device comprises a planar waveguide arranged on a substrate, and further comprises an optical coupler for coupling coherent light of a predetermined wavelength into the planar waveguide such that the coherent light propagates through the planar waveguide with an evanescent field of the coherent light propagating along an outer surface of the planar waveguide. The outer surface of the planar waveguide comprises binding sites thereon capable of binding target samples to the binding sites such that light of the evanescent field is scattered by target samples bound to the binding sites. The binding sites are arranged along a plurality of predetermined lines, the predetermined lines being arranged such that the light scattered by the target samples bound to the binding sites interferes at a predetermined detection location with a difference in optical path length which is an integer multiple of the predetermined wavelength of the light.

The detection of binding affinities according to the invention is neither limited to specific types of target samples nor to any type of binding sites, but rather the binding characteristics of molecules, proteins, DNA etc. can be analysed with respect to any type of binding sites on the planar waveguide. The detection of binding affinities can be achieved in a label-free manner. Alternatively, scattering enhancers (e.g. scattering labels) which strongly scatter the light can be used to increase the detection sensitivity. Such scattering enhancers can be a nanoparticle (alone or with a binder) or in another example a colloidal particle. The binding characteristic to be analysed can be of static type (for example, it can be analysed whether a target sample has or has not bound to the binding sites) or of dynamic type (for example, the dynamics of the binding process over time can be analysed). Binding sites are locations on the outer surface of the planar waveguide to which a target sample may bind. For example, binding sites may comprise capture molecules which are immobilized on the outer surface of the planar waveguide, or may simply comprise activated locations on the outer surface of the planar waveguide which are capable of binding target samples to the activated locations, or may be embodied in any other manner suitable to bind target samples at the desired locations on the outer surface of the planar waveguide. The plurality of predetermined lines may comprise individual separate lines or may comprise a line pattern in which the individual lines are connected to form a single line, for example a meandering single line pattern. The distance between adjacent predetermined lines along which the binding sites are arranged is chosen with respect to the predetermined wavelength of the light. Preferred distances between adjacent predetermined lines are of the order of more than 100 nm. A range of about 100 nm to about 1000 nm for the distance between adjacent predetermined lines is preferred for the use of visible light in the planar waveguide so that the scattered light can be detected by standard optical means. In addition, it is preferred that the planar optical waveguide has a high refractive index relative to the medium on the outer surface of the planar waveguide, so that the penetration depth of the evanescent field is only small and the fraction of coherent light propagating in the evanescent field is high. For example, the refractive index of the planar waveguide may be in the range of 1.6 to 2.5, whereas the refractive index of the medium at the surface of the planar waveguide is typically in the range of 1 to 1.5. By way of example, the binding sites may comprise capture molecules which are immobilised on the outer surface of the planar waveguide. The immobilized capture molecules together with the target samples bound thereto form a plurality of scattering centres scattering the coherent light of the evanescent field. The coherent light propagating along the planar waveguide has a predetermined wavelength and is preferably monochromatic (ideally at a single wavelength). Since the light of the evanescent field propagating along the surface of the planar waveguide is coherent as is the light propagating within the planar waveguide, the coherent light of the evanescent field is scattered coherently by the scattering centres formed by the target molecules bound to the capture molecules (or more generally, by the target sample bound to the binding sites) which are arranged on the different predetermined lines. The scattered light at any location can be determined by adding the contributions from each of the individual scattering centres. A maximum of the scattered light is located at the predetermined detection location because the predetermined lines are arranged such that at the predetermined detection location, the optical path length of the light scattered by the different scattering centres differs by an integer multiple of the wavelength of the light. For a maximum signal at the detection location, the optical path length of the light from the optical coupler to the predetermined lines and from there to the predetermined detection location is also a multiple integer of the predetermined wavelength. Thus the light scattered by the target samples bound to the binding sites interferes at a predetermined detection location. The requirement of constructive interference is met by any scattered light which adds to the detectable signal in the detection location. The predetermined detection location is not limited to a particular shape, for example it may have the shape of a point or a strip. The arrangement of the binding sites "along the predetermined lines" represents the optimum case in which all binding sites are exactly arranged on the predetermined lines. Such optimal arrangement of the binding sites results in a maximum signal at the detection location. It is obvious to the person skilled in the art that in practice the arrangement of the binding sites can deviate to some extent from such optimum arrangement. For example, the deviation may be caused by the method for arranging the binding sites on the outer surface of the planar waveguide, as will be explained in more detail below.

In accordance with one aspect of the device according to the invention, the distance between adjacent predetermined lines decreases in the direction of propagation of the light of the evanescent field. In general, the angles under which the scattered light of the evanescent field interferes at the predetermined detection location are different for the various scattering centres (target samples bound to the binding sites), which are arranged along the predetermined lines. Since at the predetermined detection location the scattered light is to interfere to a maximum, the difference in optical path length of the light scattered from the various scattering centres must be a multiple integer of the wavelength of the light. The decrease in distance between the adjacent predetermined lines takes account of that fact and causes the light to interfere to a maximum at the predetermined detection location, which does not need to have the shape of a point or a small spot but may also have the shape of a strip or any other desired shape.

According to a further aspect of the device according to the invention, the plurality of predetermined lines on which the binding sites are arranged comprises curved lines. The curvature of the lines is such that light of the evanescent field scattered by the target samples bound to the binding sites arranged along these predetermined lines interferes to a maximum at the predetermined detection location. The detection location preferably has the shape of a point. Each of the individual predetermined lines may have a curvature which is different from the curvature of the other predetermined lines. In practice, the detection location is not a point but may be a small spot or a strip having a length which is smaller than the length of the predetermined lines along which the binding sites are arranged. The curvature of each individual curved predetermined line is chosen such that the optical path length of the light propagating from the optical coupler to the individual predetermined line and from there to the predetermined detection location is a multiple integer of the predetermined wavelength of the propagating light for the entire curved line. This is advantageous in that also the light scattered by scattering centres located on the outer sections of the predetermined lines contributes to the signal in the spatially reduced area of the point-shaped (or spot or strip-shaped) detection location.

In accordance with still a further aspect of the device according to the invention, the plurality of predetermined lines are arranged on the outer surface of the planar waveguide in a manner such that their locations in $x_j,y_j$-coordinates are geometrically defined by the equation $$x_j = \frac{\lambda N(A_0 + j) - \sqrt{n_s^2(N^2 - n_s^2)(y_j^2 + f^2) + (n_s\lambda)^2(A_0 + j)^2}}{N^2 - n_s^2}$$

wherein

λ is the vacuum wavelength of the propagating light,

N is the effective refractive index of the guided mode in the planar waveguide; N depends on the thickness and the refractive index of the planar waveguide, the refractive index of the substrate, the refractive index of a medium on the outer surface of the planar waveguide and the polarization of the guided mode, $n_s$ is the refractive index of the substrate, f is the thickness of the substrate, $A_0$ is an integer which is chosen to be close to the product of the refractive index $n_s$ and the thickness f of the substrate divided by the wavelength λ, and j is a running integer that indicates the index of the respective line.

The chosen integer $A_0$ assigns negative x-values at the centre of the lines with negative j values and positive x-values at the centre of lines with positive j values. Or to say it in other words, the integer $A_0$ defines the origin of the x,y-coordinates frame that is used for the location of the lines at the outer surface of the planar waveguide; the chosen $A_0$ value puts the detection location at x=0, y=0, z=−f.

As already outlined above, for an improved signal at the predetermined detection location it is preferred that the plurality of predetermined lines are arranged in a manner such that the scattering centres arranged along these predetermined lines are located on a curved grid-like structure with a decreasing distance between adjacent predetermined lines. Such an arrangement fulfils the condition that the difference in optical path length for the light propagating from the optical coupler to the individual predetermined lines and scattered by the scattering centres to the predetermined detection location is a multiple integer of the predetermined wavelength of the light propagating in the waveguide. Also, the optical path length of the light propagating from the optical coupler to the individual predetermined lines and from there to the predetermined detection location is a multiple integer of the predetermined wavelength of the propagating light for the entire curved line. Thus, it is possible to form a compact device due to the binding sites being arranged on the surface of the planar waveguide while the detection location may be formed at the bottom surface of the substrate carrying the planar waveguide.

Two embodiments are particularly envisaged of how the binding sites can be arranged along the plurality of predetermined lines. According to a first embodiment, the binding sites comprise capture molecules attached to the surface of the planar waveguide along the predetermined lines only. These capture molecules are capable of binding the target samples and are immobilized on the outer surface of the planar waveguide (although, as mentioned above, the binding sites can be formed by the activated surface of the planar waveguide itself). Immobilizing the capture molecules on the outer surface of the planar waveguide along the predetermined lines can generally be performed by any suitable method, for example it may be performed using photolithographic methods using a lithographic mask with curved lines. It goes without saying, that the arrangement of the binding sites along the predetermined lines is to be understood in any embodiment of the invention in a sense that the majority of the binding sites—in the instant embodiment the capture molecules—are located along the predetermined lines and does explicitly include that some binding sites are arranged at locations different therefrom.

According to a second embodiment, the binding sites again comprise capture molecules capable of binding the target samples, which is no restriction to a certain type of binding site or a certain type of target sample. The capture molecules are again capable of binding the target samples. However, the arrangement of capture molecules capable of binding the target molecules along the predetermined lines is performed by dispensing and immobilizing capture molecules capable of binding the target samples on the (entire) surface of the planar waveguide, and by subsequently deactivating those capture molecules which are not arranged along the predetermined lines. The term "deactivating" in this respect refers to any suitable method for changing the binding capability of the capture molecules (for example by exposing the capture molecules to light for a predetermined time) in order to achieve that they are no longer capable of binding target samples. According to this embodiment of the invention, the capture molecules can be applied uniformly or statistically onto the outer surface of the planar waveguide. After deactivation of capture molecules which are arranged between the predetermined lines only the capture molecules arranged along the predetermined lines (these have not been deactivated) are capable of binding a target sample. Nevertheless, the deactivated capture molecules remain immobilized on the outer surface of the planar waveguide.

This embodiment has the additional advantage that the contribution of the signal generated by the light scattered by target molecules bound to capture molecules to the overall signal at the detection location is increased. Generally, the difference between the signals of the light scattered by the target molecules bound to the captures molecules and the light scattered by the capture molecules without any target molecules bound thereto is small compared to the light scattered by the capture molecules alone. Assuming that the scattering properties of the capture molecules arranged along the predetermined lines (which have not been deactivated) and of the deactivated capture molecules arranged between the predetermined lines are identical and further assuming that the capture molecules are homogeneously distributed over the outer surface of the planar waveguide, then ideally no signal is produced at the detection location after the capture molecules have been immobilized on the outer surface of the planar waveguide and after the capture molecules arranged between the predetermined lines have been deactivated. In practice, however, deactivation of the capture molecules slightly changes the scattering properties of the capture molecules, so that it may not be ideal to deactivate all of the capture molecules which are arranged between the predetermined lines. Instead, only the vast majority of the capture molecules arranged between the predetermined lines may be deactivated. Deactivation of the capture molecules is performed to an extent such that the overall signal at the detection location produced by those capture molecules arranged along the predetermined lines and by those deactivated and the few non-deactivated capture molecules arranged between the predetermined lines is at a minimum, and is preferably zero. Assuming that the signal so obtained at the detection location can be reduced to zero this means, that after adding the target samples the signal produced at the detection location only results from target samples bound to the capture molecules. In case no target samples are bound to the capture molecules, the signal at the detection location remains zero. This increases the sensitivity of the detector for the signal generated by the light scattered by the target molecules bound to the capture molecules at the detection location.

In accordance with a further aspect of the device according to the invention, the planar waveguide has a refractive index $n_w$ which is substantially higher than the refractive index $n_s$ of the substrate and which is also substantially higher than the refractive index $n_{med}$ of the medium on the outer surface of the planar waveguide, such that for a predetermined wavelength of the light the evanescent field has a penetration depth in the range of 40 nm to 200 nm. The term "substantially higher" shall be understood as designating a difference in refractive index allowing a coupling in of the light into the planar waveguide where it propagates under total reflection. The light propagating along the planar waveguide has an evanescent field which propagates along the outer surface of the planar waveguide. The evanescent field has a penetration depth which depends on the index $n_{med}$, the effective refractive index N of the guided mode, as well as on the wavelength of the propagating light, so that the penetration depth can be adapted such that the light of the evanescent field is coherently scattered by the target samples bound to the binding sites located on (or in proximity) to the predetermined lines on the outer surface. The approximate values of the penetration depth mentioned above are to be understood to explicitly include the exact boundary values thereof.

In accordance with a further aspect of the device according to the invention, the device comprises a further optical coupler for coupling out the light that has propagated through the planar waveguide. Both, the optical coupler for coupling the light into the planar waveguide as well as the further optical coupler for coupling out the light that has propagated through the planar waveguide may comprise an optical grating for coherently coupling light into and out of the planar waveguide. The optical coupler and the further optical coupler comprise an optical grating for coherently coupling light into and out of the planar waveguide under a respective predetermined in-coupling angle or out-coupling angle. The in-coupling angle or out-coupling angle is determined by the wavelength of the light as well as by the characteristic of the optical coupler. However, within the scope of the invention the light can also be coupled into and out of the planar waveguide by any other means suitable for coupling light into and out of a planar waveguide of a thickness in the range of some nanometers to some hundred nanometers. Only by way of example, an alternative optical coupler may be an optical prism.

In accordance with a further aspect of the device of the invention, the planar waveguide has a first end section and a second end section which are arranged at opposite ends of the planar waveguide with respect to the direction of propagation of the light through the planar waveguide. The first end section and the second end section comprise a material which is absorptive at the wavelength of the light propagating through the planar waveguide. The absorptive material minimizes reflections of the light propagating along the planar waveguide towards the respective end section and back into the planar waveguide. This improves the detected signal as light which may have been reflected from the ends of the planar waveguide is eliminated or at least greatly minimized.

In accordance with a further aspect of the device according to the invention, a plurality of measurement zones are arranged on the outer surface of the planar waveguide. In each measurement zone the binding sites are arranged along the plurality of predetermined lines. For high-throughput screening, the simultaneous detection of binding affinities of a sample can be achieved for different types of binding sites and target samples by arranging the respective target samples bound to the binding sites in separate measurement zones. Each measurement zone has a corresponding individual detection location to allow a separate detection of the scattered light of the evanescent field.

In accordance with a further aspect of the device according to the invention, the plurality of measurement zones comprises measurement zones of different sizes. All sizes of the measurement zones are known. At the respective detection location, the light scattered in corresponding measurement zones of different size in which the same type of target samples is bound to the same type of binding sites can be compared. The intensity of the scattered light at the detection location has a quadratic correlation to the number of scattering centers in the respective measurement zone on the planar surface of the waveguide. Thus, for a uniform distribution and areal density of scattering centers in the measurement zones of different sizes, the intensities of the scattered light at the respective detection locations of corresponding measurement zones of different sizes have a quadratic correlation to the size of the respective measurement zones. Therefore, the intensities of the scattered light at detection locations of measurement zones of different sizes can be used to verify that the measured intensities are indeed representative of light scattered by the scattering centers arranged on the predetermined lines.

According to an aspect of the invention, each measurement zone has an area larger than 25 $\mu m^2$, wherein the plurality of predetermined lines has a distance between adjacent predetermined lines less than 1.5 μm, in particular less than 1 μm. This allows to achieve highly integrated devices with high numbers of measurement zones, i.e. 1000, 10000, 100000, . . . , up to $4 \times 10^6$ measurement zones per square centimetre.

Advantageously, the binding sites are arranged along at least two pluralities of predetermined lines in a single measurement zone. Each of the two pluralities of predetermined lines is arranged such that the light scattered by the target samples bound to the binding sites arranged along the respective plurality of predetermined lines interferes with a difference in optical path length which is an integer multiple of the predetermined wavelength of the light at an individual detection location for each of the plurality of predetermined lines. The individual detection locations are spatially separated from each other. More than one plurality of predetermined lines in the measurement zone which are arranged so as to provide spatially separated detection locations allow carrying out additional methods for the detection of binding events (e.g. the detection of cooperative bindings or the detection of reaction cascades).

In accordance with another aspect of the device according to the invention, the device comprises a diaphragm having an aperture which is arranged such that light at the detection location is allowed to pass through the aperture while light at a location different from the detection location is blocked by the diaphragm. A mechanical diaphragm as well as an electronic diaphragm can be adapted to blind out all light other than that being scattered to the detection location. Advantageously, the diaphragm can be formed on the outer surface of the substrate on that side remote from the planar waveguide. For example, a non-transparent material, e.g. a chromium layer, can be applied to the surface of the substrate remote to the waveguide. The non-transparent chromium layer has a transparent aperture at the detection location through which the light scattered to the detection location can pass while the rest of the light not scattered to the aperture is blocked.

In accordance with a still further aspect of the device according to the invention, the diaphragm further comprises at least one further aperture which is arranged adjacent to the aperture when viewed in the direction of propagation of the light through the planar waveguide. The further aperture is located adjacent the aperture such that incoherent light scattered to the further aperture may pass through the further aperture. Advantageously, the detected incoherent background light can be corrected by the use of a diaphragm having a further aperture. The further aperture does not itself detect the incoherent background light at the detection location but allows determination of the amount of the incoherent light at the detection location from a measurement of the incoherent light at a location different from the detection location. The so determined amount of incoherent light at the detection location cannot be separated from the light at the detection location, but can be subtracted from the entire signal at the detection location once the entire signal at the detection location has been measured by a detector. For an improved correction a first further aperture is located with respect to the direction of the propagating light in front of the detection location and a second further aperture is located behind the detection location. Such a configuration allows detecting an average value for the incoherent light at the detection location for correcting the signal at the detection location.

Another aspect of the invention relates to a system for the detection of binding affinities comprising a device for the detection of binding affinities according to the invention. The system further comprises a light source for emitting coherent light of a predetermined wavelength, the light source and the device being arranged relative to one another such that the coherent light is coupled into the planar waveguide via the optical coupler. Alternatively, the system further comprises optical means for scanning and/or adjustment of the angle of light impinging on the optical coupler since the exact coupling angle of the optical coupler can vary from device to device. Alternatively, the wavelength of the light emitted by the light source in the system can be tuned which may be advantageous in case the angle of the light impinging on the optical coupler is fixed for constructional reasons.

According to still another aspect of the system according to the invention, the system further comprises an optical imaging unit, the optical imaging unit being focused such as to produce an image of the detection location of the device. The optical imaging unit is capable of providing an image of the predetermined detection location in which the light scattered by the target samples bound to the binding sites interferes with a difference in optical path length which is an integer multiple of the predetermined wavelength of the light. The optical imaging unit can be used for imaging the light present at the detection location to an observation location. The optical imaging unit can be adapted for imaging both the light from the detection location as well as the light from the further aperture or further apertures, since this light may be used for subtraction of the incoherent background light from the entire light present at the detection location. Alternatively or in addition, the optical imaging unit can be used to select only the light at the detection location by focusing the optical imaging unit to the detection location. A diaphragm is then no longer needed.

Another aspect of the invention relates to a method for detection of binding affinities. The method comprises the steps of:

providing a device comprising a planar waveguide arranged on a substrate and an optical coupler, coupling coherent light of a predetermined wavelength into the planar waveguide such that the coherent light propagates along the planar waveguide with an evanescent field of the coherent light propagating along an outer surface of the planar waveguide, attaching target samples to binding sites arranged along a plurality of predetermined lines on the outer surface of the planar waveguide, detecting, at a predetermined detection location, light of the evanescent field scattered by target samples bound to binding sites arranged along the predetermined lines, the light scattered by the target samples bound to the binding sites having, at the predetermined detection location, a difference in optical path length which is an integer multiple of the predetermined wavelength of the light.

BRIEF DESCRIPTION OF THE DRAWINGS

Further advantageous aspects of the invention become apparent from the following description of embodiments of the invention with reference to the accompanying schematic drawings in which.

DETAILED DESCRIPTION

Figure 1:
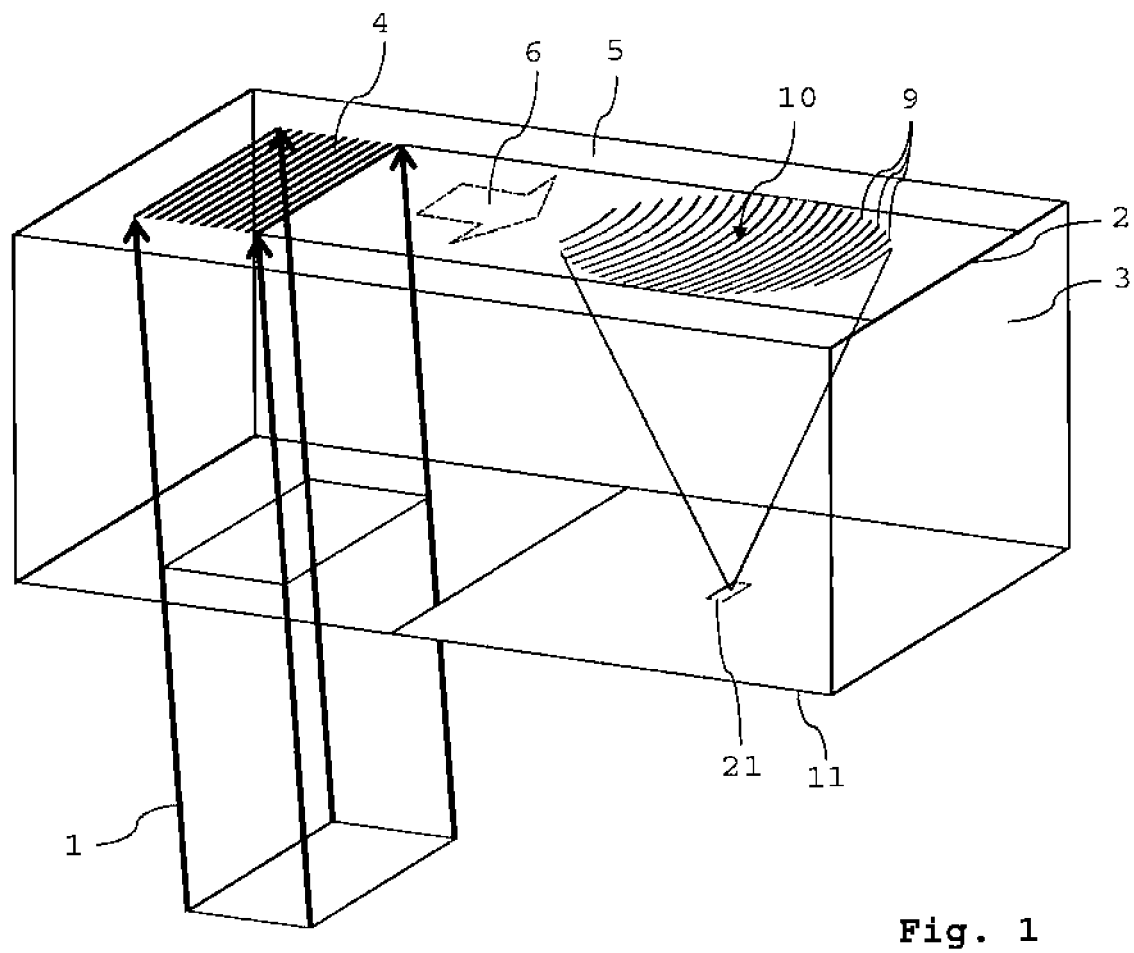
FIG. 1 shows a perspective view of an embodiment of the device according to the invention.

FIG. 1 shows a perspective view of an embodiment of the device according to the invention for the detection of binding affinities of a sample. The device comprises a substrate 3 of a transparent material which in the embodiment shown has the shape of a rectangular cube, without being limited to this shape. A planar waveguide 2 (see also FIG. 2) is arranged on the upper side of the substrate 3, into which a coherent light 1 is coupled such that the coherent light propagates through the planar waveguide 2 under total reflection. Since the planar waveguide 2 has a thickness in the range of some nanometers to some hundred nanometers only, it is not illustrated as a separate layer in FIG. 1, but is shown exaggerated in FIG. 2. As illustrated by the parallel arrows in FIG. 1, coherent light 1 of a predetermined wavelength is coupled through the substrate 3 into the planar waveguide 2 with the aid of a grating 4 acting as an optical coupler. The coherent light coupled into the planar waveguide 2 propagates along the planar waveguide 2 with an evanescent field 6 (represented by an arrow) penetrating into the medium above the upper surface of the planar waveguide 2 (see again FIG. 2). The evanescent field 6 propagates along the outer surface 5 of the planar waveguide 2. A measurement zone 10 arranged on the outer surface of the planar waveguide 2 comprises a plurality of predetermined lines 9 (each of the shown lines represent a multiplicity of lines, in particular fifty lines in the present example of such a device; and only one such measurement zone being shown in FIG. 1 for the sake of clarity). Binding sites (not shown in FIG. 1) to which target samples can bind are arranged along these predetermined lines 9. Coherent light of the evanescent field 6 is scattered by the target samples bound to binding sites within the measurement zone 10. Some of the light scattered by the target samples bound to binding sites is directed to a detection location where a diaphragm 11 comprising an aperture 21 is arranged. The diaphragm 11 is made from a non-transparent material and may for example be a chromium layer which is applied onto the lower surface of the substrate 3.

Figure 2:
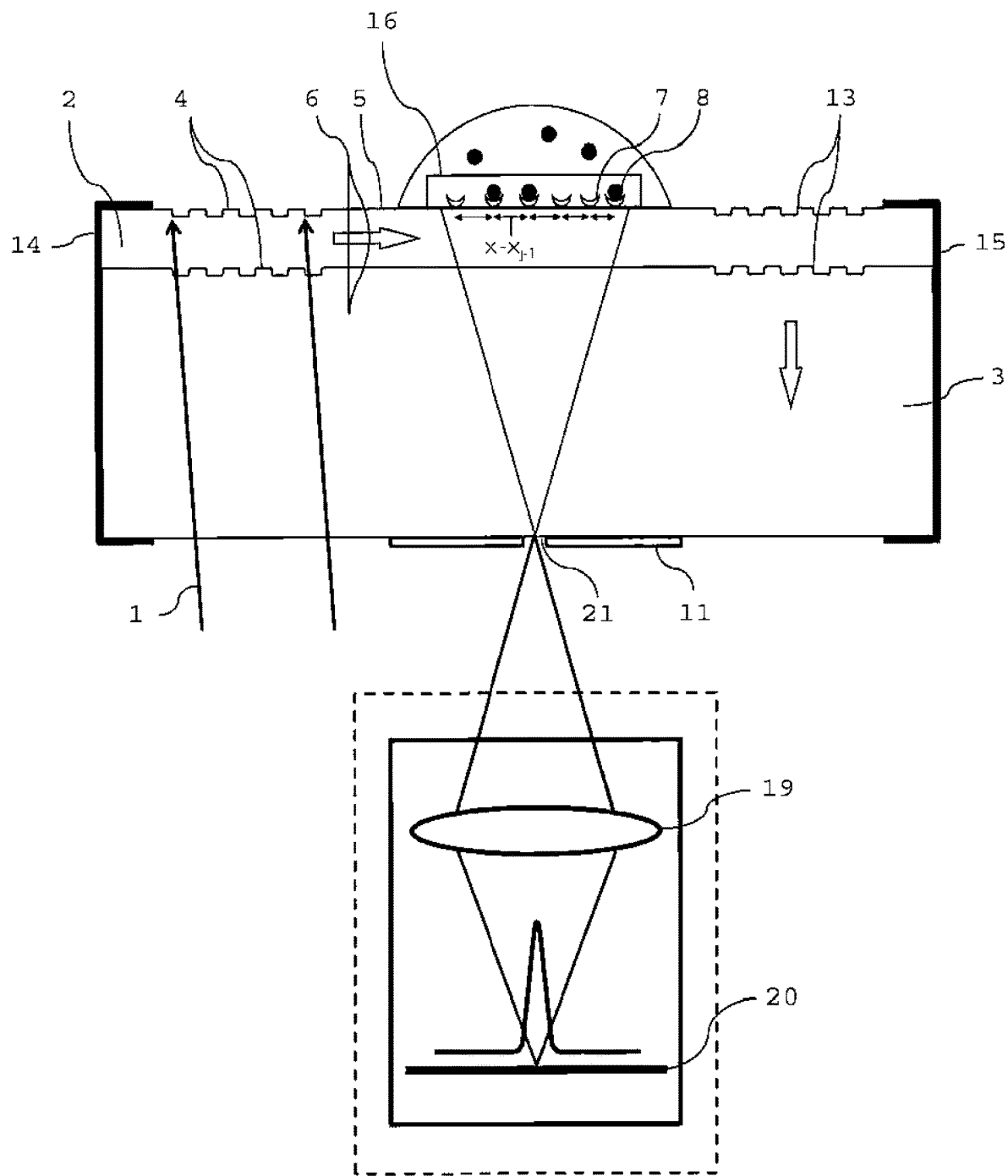
FIG. 2 shows a sectional view of the device of FIG. 1.

FIG. 2 shows a sectional view of the device of FIG. 1 with the thickness of the planar waveguide being shown exaggerated for the purpose of explaining the general working principle. As can be seen, the light coupled into the planar waveguide 2 with the aid of optical grating 4 propagates through the planar waveguide 2 under total reflection until reaching a further grating 13 arranged at the opposite end of the planar waveguide 2. This further grating serves as a further optical coupler to couple the light out of the planar waveguide. To avoid reflections and for minimizing incoherent background light, a first end section 14 and a second end section 15 of the planar waveguide 2 comprise an absorptive material. Corresponding to the light propagating in the planar waveguide, the evanescent field 6 propagates along the outer surface 5 of the planar waveguide 2.

The refractive index $n_w$ of the planar waveguide 2 is substantially higher than the refractive index $n_s$ of the substrate 3 and also substantially higher than the refractive index $n_{med}$ of the medium on the outer surface 5 of the planar waveguide 2. The refractive index $n_{med}$ of the medium on the outer surface 5 may vary depending on the type of sample applied thereto. For example, the refractive index $n_{med}$ for the medium on the outer surface 5 can be of the order of the refractive index of water in case the target sample is present in an aqueous solution applied to the outer surface 5 of the planar waveguide 2, or may be of the order of the refractive index of air in case of dry target samples, or may be in the order of the refractive index of a hydrogel layer 16 in case the binding sites to which target samples 8 can bind are contained in a hydrogel layer 16 on the outer surface 5. The penetration depth of the evanescent field 6 into the medium on the outer surface 5 of the planar waveguide 2 (distance between the outer surface 5 of the planar waveguide 2 and the $1/e^2$ intensity descent of the evanescent field 6) depends on the index $n_{med}$ of the medium on the outer surface 5 of the planar waveguide 2, the effective refractive index N of the guided mode and on the wavelength λ of the light.

The light in the evanescent field 6 propagating along the outer surface 5 of the planar waveguide 2 is scattered by target samples 8 bound to binding sites, and these binding sites may comprise capture molecules 7 which are capable of binding the target samples 8 and which are arranged in the measurement zone 10 along the predetermined lines 9 (FIG. 1). In FIG. 2 it is indicated by arrows of decreasing length, that the distance between adjacent predetermined lines along which the capture molecules 7 are arranged decreases when viewed in the direction of propagation of the light. As can further be seen, in the embodiment shown in FIG. 2 the target samples 8 have been applied to the measurement zone by dispensing a droplet containing the target samples 8. Some of the light scattered by the target samples 8 bound to the capture molecules 7 is directed to the detection location where the aperture 21 of diaphragm 11 is arranged. As an option, the light at the detection location can be imaged on a photo-detector 20 by an optical imaging unit 19. The optical imaging unit 19 and the photo-detector 20 are shown surrounded by a box drawn in dashed lines, since they can be provided alternatively or in combination, and can in particular be provided in combination in one unit.

Figure 3:
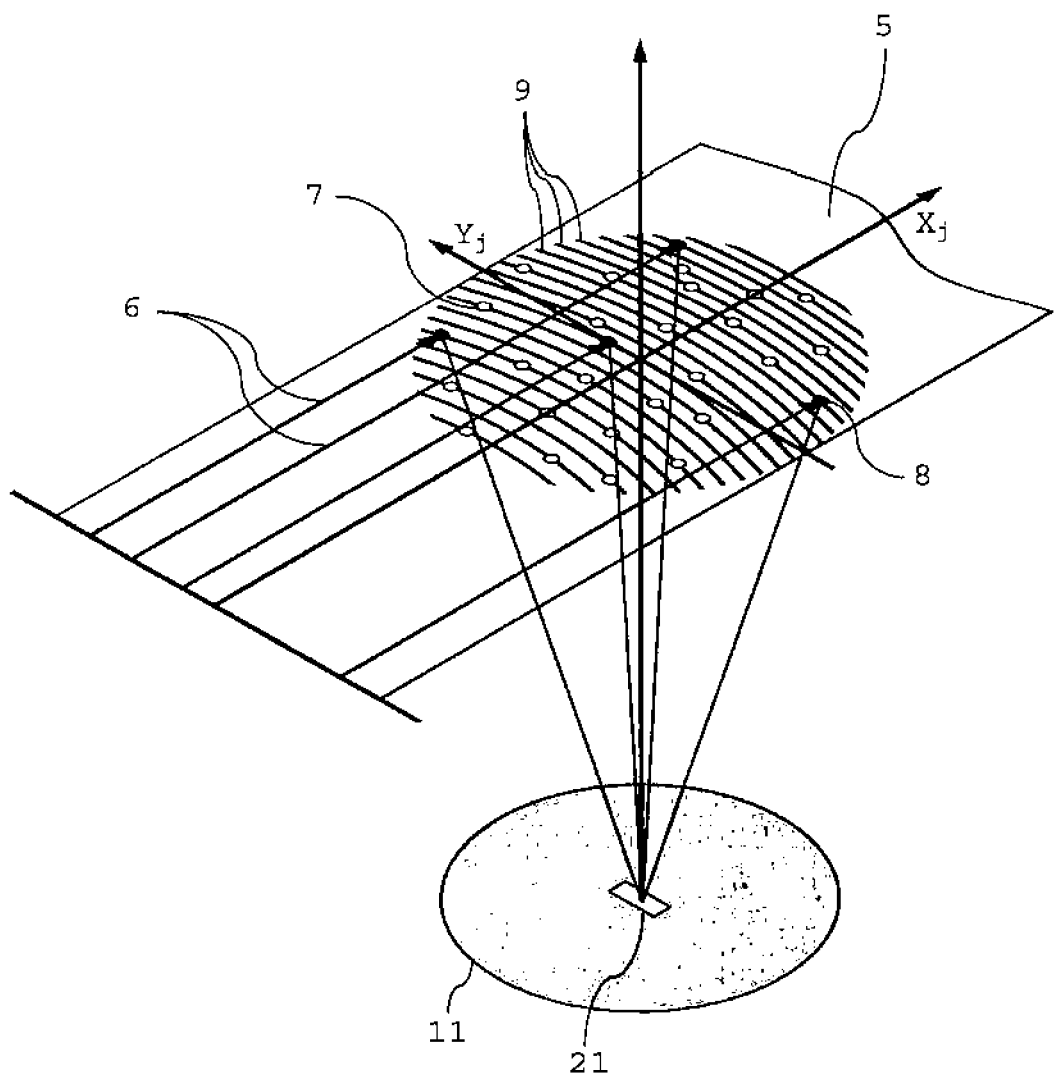
FIG. 3 shows an illustration of different optical paths for the light of the evanescent field propagating along the outer surface and being scattered to the detection location.

While it is already evident from FIG. 2 that the lengths of the optical paths of the light of the evanescent field 6 which is scattered by target samples 8 bound to different capture molecules 7 to the detection location is different, this becomes even more clear when glancing at FIG. 3 in which a number of such different optical paths are explicitly shown. Some of the coherent light of the evanescent field 6 is scattered by the target samples 8 bound to different capture molecules 7 in a manner such as to interfere at the detection location which is the location of the aperture 21 of diaphragm 11. For a predetermined detection location, the arrangement and geometry of the predetermined lines 9 as well as the thickness of the substrate 3 are selected such that at the detection location the difference in optical path length is an integer multiple of the predetermined wavelength of the coherent light. Thus, the interference of the light at the detection location is the coherent additive superposition of the light scattered to the detection location by the target molecules 8 bound to the different capture molecules 7.

For the embodiment shown in FIG. 3 the plurality of predetermined curved lines 9 are arranged on the outer surface 5 of the planar waveguide in a manner such that their locations in the plane of the outer surface 5 of the planar waveguide are geometrically expressed in $x_j, y_j$-coordinates by the equation $$x_j = \frac{\lambda N(A_0 + j) - \sqrt{n_s^2(N^2 - n_s^2)(y_j^2 + f^2) + (n_s\lambda)^2(A_0 + j)^2}}{N^2 - n_s^2}$$

wherein

λ is the vacuum wavelength of the propagating light,

N is the effective refractive index of the guided mode in the planar waveguide; N depends on the thickness and the refractive index of the planar waveguide, the refractive index of the substrate, the refractive index of a medium on the outer surface of the planar waveguide and the polarization of the guided mode, $n_s$ is the refractive index of the substrate, f is the thickness of the substrate, $A_0$ is an integer which is chosen to be close to the product of the refractive index $n_s$ and the thickness f of the substrate divided by the wavelength λ, and j is a running integer that indicates the index of the respective line.

Figure 4:
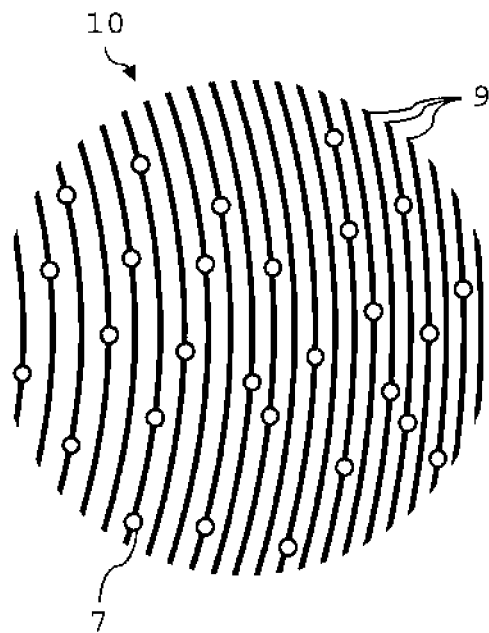
FIG. 4 shows a measurement zone of the device according to the invention comprising an arrangement of a plurality of predetermined lines, with binding sites being immobilized along the predetermined lines.
Figure 5:
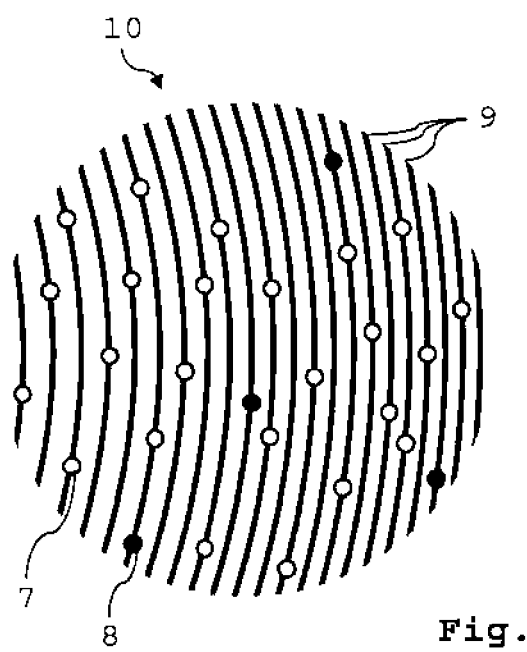
FIG. 5 shows the measurement of FIG. 4, with some target samples being bound to the binding sites.

FIG. 4 shows a measurement zone 10 in an enlarged view comprising the predetermined lines 9 and binding sites represented by capture molecules 7 which are immobilized on the outer surface of the planar waveguide 5 (see FIG. 1) along the predetermined lines 9. Immobilizing the capture molecules 7 along the predetermined lines only can be performed with the aid of lithographic techniques, as this has been discussed above. In FIG. 5 target samples 8 are bound to some of the capture molecules 7. Since the capture molecules 7 are arranged along the plurality of predetermined lines 9, target samples 8 bound to the capture molecules 7 are arranged along the plurality of predetermined lines 9, too. At the detection location this results in the coherent additive superposition of the light scattered by the scattering centres formed by the target samples 8 bound to the capture molecules 7, as this has been explained above.

Figure 6:
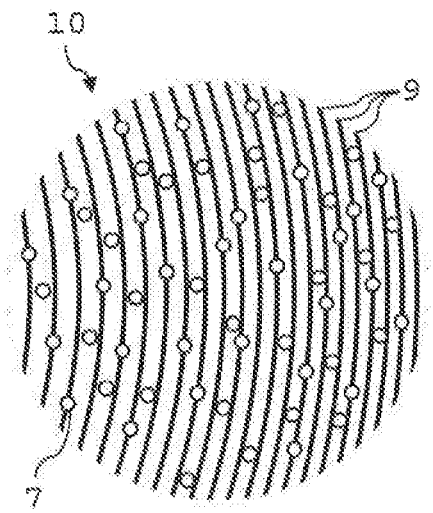
FIG. 6 shows a measurement zone of a device according to the invention comprising an arrangement of a plurality of predetermined lines, with binding sites being immobilized along the predetermined lines and between the predetermined lines.
Figure 7:
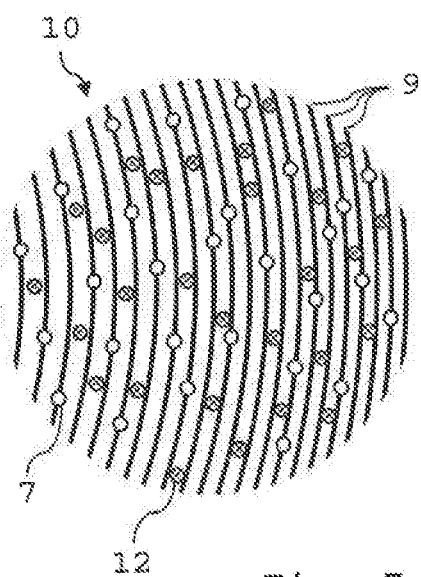
FIG. 7 shows the measurement zone of FIG. 6, with those binding sites arranged between the predetermined lines being deactivated.
Figure 8:
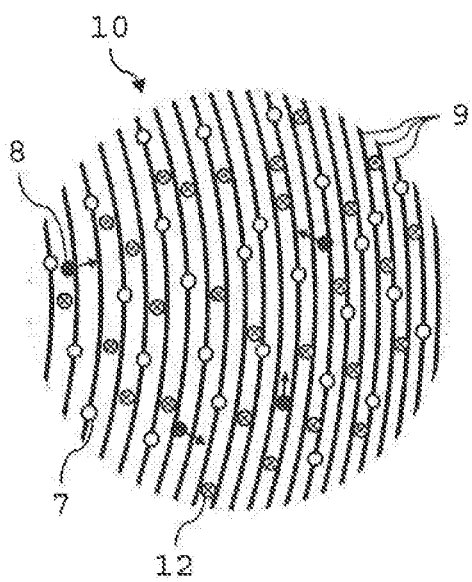
FIG. 8 shows the measurement zone of FIG. 7 with the target samples being added.

FIG. 6, FIG. 7, FIG. 8 and FIG. 9 show again a measurement zone 10 in an enlarged view. However, the manner how the capture molecules 7 capable of binding the target samples 8 have been immobilized along the predetermined lines 9 is different.

As can be seen in FIG. 6, in a first step the capture molecules 7 are immobilised over the (entire) outer surface of the planar waveguide in the measurement zone 10, so that there is no arrangement of the capture molecules along the plurality of predetermined lines 9. Thus, the light of the evanescent field scattered by the capture molecules 7 does not interfere at the detection location in the manner described above.

As can be seen in FIG. 7, the capture molecules arranged between the predetermined lines 9 have been deactivated so that no target samples can bind to these deactivated capture molecules 12 anymore. Accordingly, the only capture molecules 7 capable of binding target samples are arranged along the plurality of predetermined lines 9. The accuracy of the immobilization of the capture molecules 7 along the predetermined lines 9 depends on the method of attaching, immobilizing or deactivating the capture molecules 7. As a result, the location of the immobilized capture molecules 7 capable of binding the target samples 8 may not be exactly "on" the predetermined lines 9 but may to some extent deviate from the exact location "on" the predetermined lines 9. In practice, the deviation from the exact location "on" the predetermined lines may be within a range which is smaller than a quarter of the distance of adjacent predetermined lines 9. This results in a still constructive interference of the light scattered to the detection location.

As has been explained in the introductory part, deactivation of the capture molecules 12 arranged between the predetermined lines 9 is performed such that after deactivation the overall signal at the detection location (no target samples 8 have been added yet) produced by the deactivated capture molecules 12 and the capture molecules 7 capable of binding the target samples 8 is set or adjusted to a tuned minimum signal at the detection location, ideally to zero.

Figure 9:
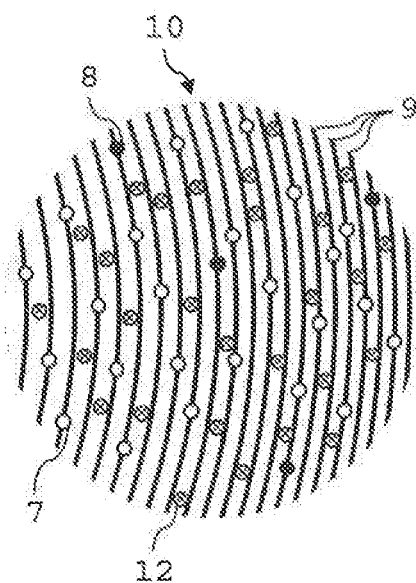
FIG. 9 shows the measurement zone of FIG. 8 with the target samples being bound to the binding sites immobilized along the predetermined lines.

The next step is adding the target samples 8 to the measurement zone 10 on the outer surface of the planar waveguide, as this is shown in FIG. 8. Since only the capture molecules 7 arranged along the predetermined lines 9 are capable of binding the target samples 8, the target samples 8 are bound to those capture molecules 7 along the predetermined lines 9, as this is shown in FIG. 9. Due to the tuned signal at the detection location caused by the deactivated capture molecules 12 and the capture molecules 7 having been set or adjusted to a minimum before (see above), the signal at the detection location is then mainly (or entirely, if the signal produced by deactivated capture molecules and the capture molecules has been reduced to zero before) caused by the light scattered by the target samples 8 bound to the capture molecules 7 arranged along the predetermined lines.

Figure 10:
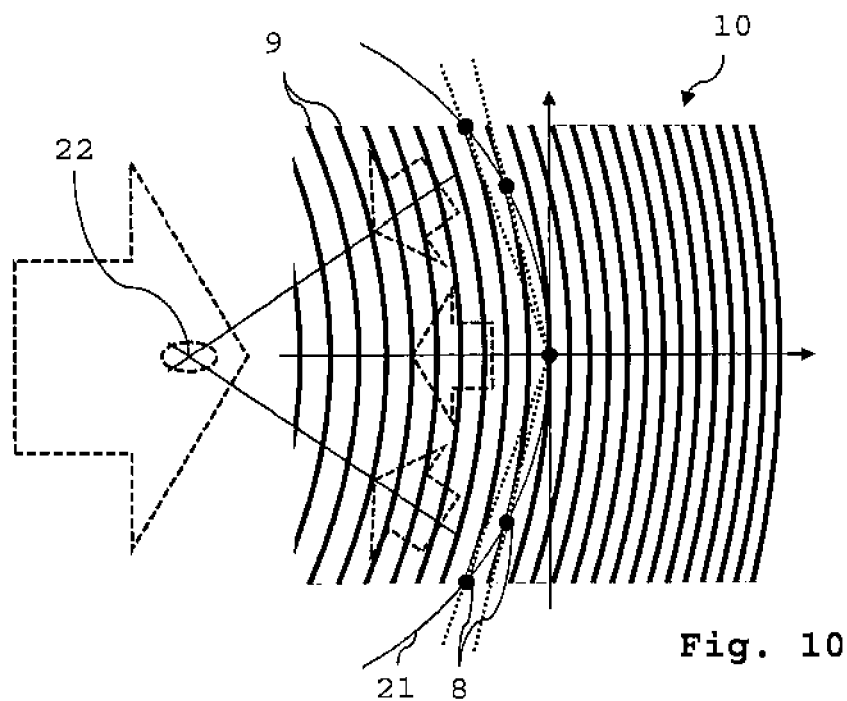
FIG. 10 shows an illustration of the construction of a blank section in which the predetermined lines of a measurement zone are to be eliminated.

FIG. 10 shows a portion of measurement zone 10 as described above for illustrating the construction of a blank section in which the predetermined lines 9 are to be eliminated to avoid second order Bragg reflections in the planar waveguide. Bragg reflections are to be avoided since they result in a reduction in intensity of the light propagating along the planar waveguide. This is particularly disadvantageous in case a plurality of measurement zones 10 is arranged one after the other on the outer surface of the planar waveguide in the direction of the propagating light. Thus, a decrease of the intensity of the propagating light scattered in the subsequent measurement zones is not only due the described scattering processes in the various measurement zones but additionally decreases due to Bragg reflections in the planar waveguide. Since in each of the measurement zones the predetermined lines 9 in a circular section of the measurement zone have a distance between adjacent lines which fulfils the condition for second order Bragg reflection, the Bragg reflection of second order in the planar waveguide defines a further location 22 at which the Bragg reflected light constructively interferes. In the shown example, the intersection points of the shown arc of circle 21 with the predetermined lines 9 indicates those locations of the predetermined lines 9 for which the Bragg condition is exactly fulfilled, so that light is reflected back and interferes constructively at the further location 22. This reflected light is not available for scattering in subsequently arranged measurement zones 10.

Figure 11:
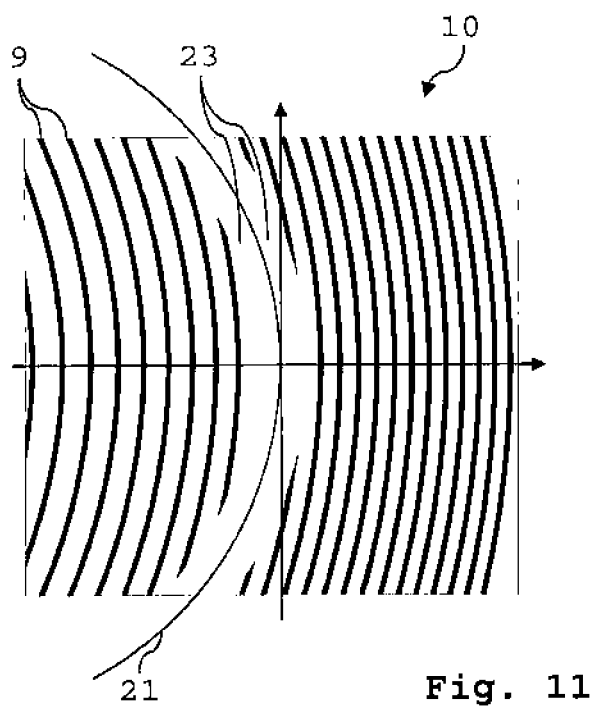
FIG. 11 shows the measurement zone of FIG. 10, with a blank section in which the predetermined lines are eliminated.

FIG. 11 shows a measurement zone 10 comprising a region 23 in proximity to the arc of circle 21 where the predetermined lines 9 are eliminated to avoid such second order Bragg reflections.

Figure 12:
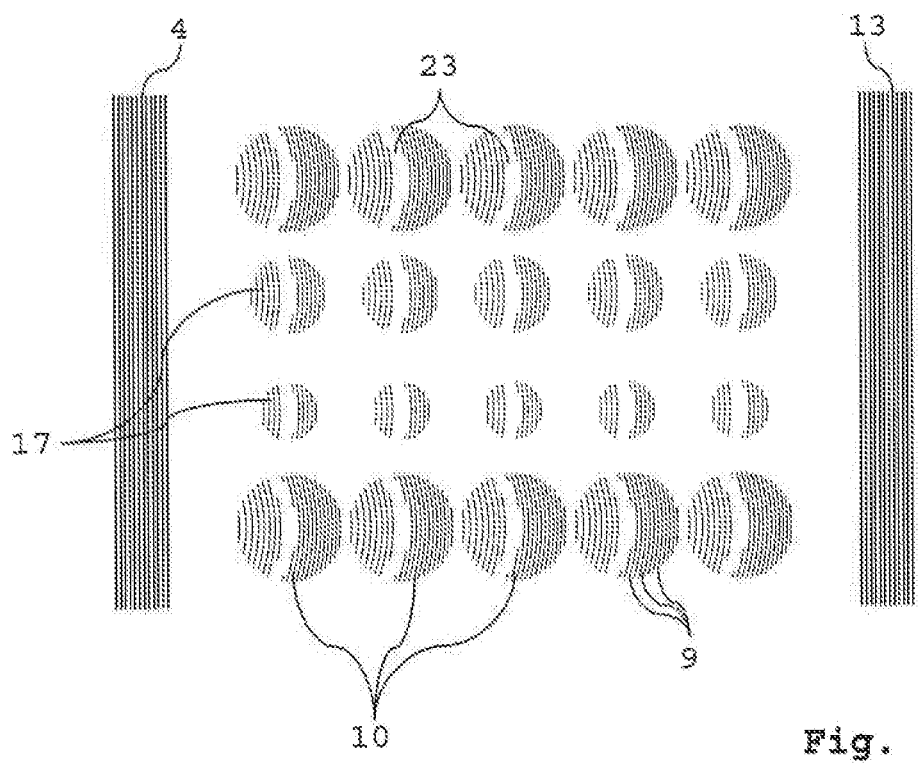
FIG. 12 shows a top view of a further embodiment of the device according to the invention comprising a plurality of measurement zones.
Figure 13:
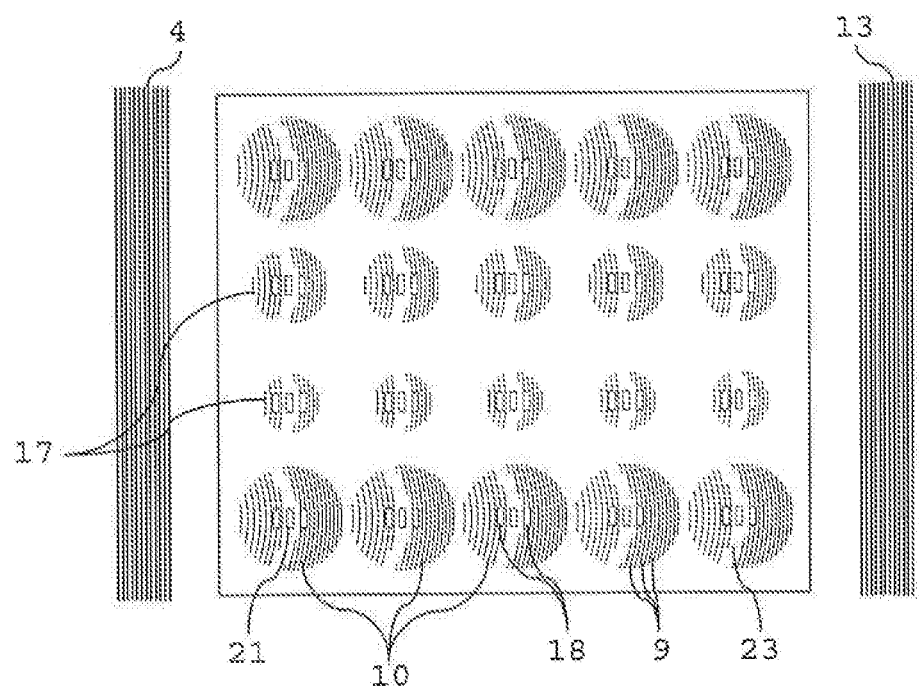
FIG. 13 shows a bottom view of the embodiment of the device of FIG. 10, with an aperture being provided at the detection location and two further apertures being provided at locations before and behind the detection location for each measurement zone.
Figure 14:
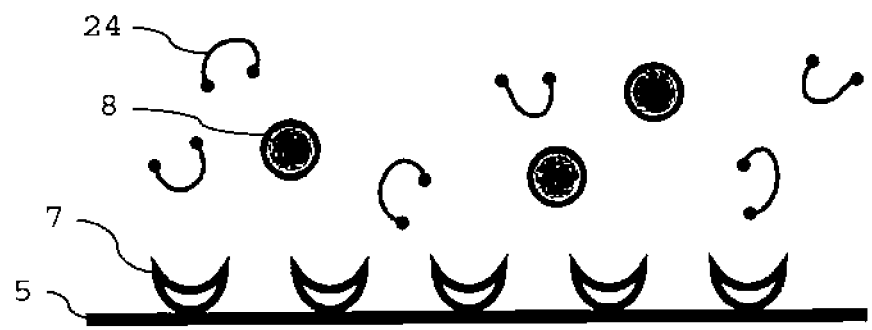
FIGS. 14-17 show a portion of a measurement zone of a device according to the invention in different phases of a process of binding target samples.
Figure 15:
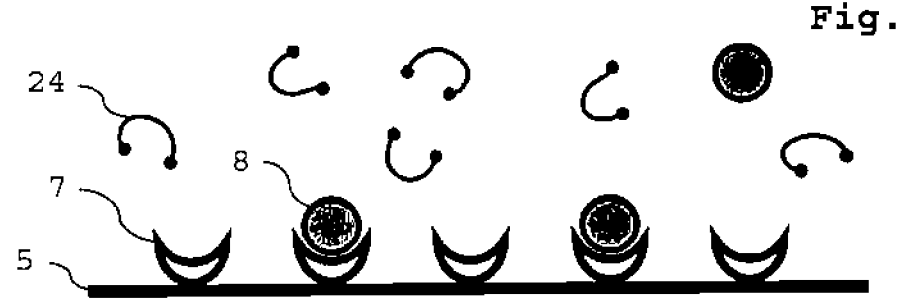
Figure 16:
Figure 17:
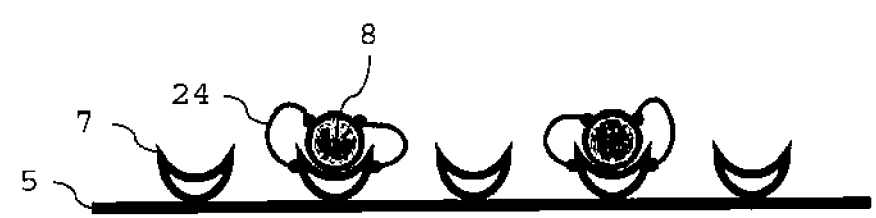

FIG. 12 and FIG. 13 show top and bottom views of a further embodiment of the device according to the invention. This embodiment of the device comprises a plurality of measurement zones 10 of a first size and measurement zones 17 of a different size. Each measurement zone 10 comprises a region 23 in which the plurality of predetermined lines 9 is eliminated to avoid Bragg reflections (see above). Generally, it is also possible that the measurement zones do not comprise the regions 23. An optical grating 4 for coupling light into the planar waveguide and a further grating 13 for coupling the light out of the planar waveguide are provided. Between the optical grating 4 and the further optical grating 13 a plurality of measurement zones 10 of the first size and of measurement zones 17 of different size are arranged where binding sites are arranged along the predetermined lines 9, as this has been discussed in detail above. The plurality of measurement zones 10 of the first size and the plurality of measurement zones 17 of different size allows the simultaneous detection of different combinations of target samples and binding sites, so that a plurality of combinations of target samples and binding sites can be analysed simultaneously with respect to the binding affinity of specific target samples to specific binding sites. Alternatively, redundant measurements can be carried out for the same combinations of target samples and binding sites.

From the bottom view of FIG. 13 it can be seen that an aperture 21 is provided for each measurement zone at the detection location, where the scattered light has a difference in optical path length which is a multiple integer of the wavelength of the light propagating in the waveguide to the scattering centre on a predetermined line and from there to the predetermined detection location, as this has also been discussed in detail above. It goes without saying that an optical imaging unit may be provided as this has been discussed in detail with respect to FIG. 2.

The measurement zones 17 of different size are arranged in between the measurement zones 10. The measurement zones 17 have a known size different from the size of the measurement zone 10, all sizes being known. At the respective detection location, the light scattered in measurement zones 10 and in corresponding measurement zones 17 can be compared (for the same type of target sample bound to the same type of binding sites). The intensity of the scattered light at the detection location has a quadratic correlation to the number of scattering centers in the measurement zone on the planar surface of the waveguide. Assuming a uniform distribution and areal density of scattering centers in the measurement zones of different sizes, the intensities of the scattered light at the respective detection locations of corresponding measurement zones of different sizes has a quadratic correlation to the size of the respective measurement zones. Accordingly, the intensities of the scattered light at detection locations of measurement zones of different sizes can be used to verify that the measured intensities are indeed representative of light scattered by the scattering centers arranged on the predetermined lines.

For an improved detection of binding affinities, two further apertures 18 are formed on the substrate 3 in front of and behind each aperture 21 dedicated to the respective measurement zone 10. As the coherent light propagating through the planar waveguide 2 might be also incoherently scattered along its way through the planar waveguide 2, a contribution of this incoherently scattered light is also detected at the detection location through the aperture 21. The apertures 18 in front of and behind aperture 21 at a predetermined distance allow for determine an average signal representative of this incoherently scattered light which can be used to correct the detected signal at the detection location by subtracting the average signal of the incoherent light from the overall signal detected at the detection location. This correction of the signal at the detection location is particularly advantageous in combination with the afore-mentioned reduction of the background signal caused by the scattering at the binding sites without any target molecules attached thereto.

FIG. 14 to FIG. 17 show a portion of a measurement zone which is formed on the outer surface 5 of a planar waveguide according to the invention. Different phases of a process of binding target samples 8 to capture molecules 7 are shown. In this process the binding of target samples 8 to capture molecules 7 is enhanced. The capture molecules 7 are immobilised at the outer surface 5. Subsequently, target samples 8 and linkers 24 are applied. The applied target samples 8 are allowed to bind to capture molecules 7 until an equilibrium condition is reached in which binding of target samples 8 to capture molecules 7 and release of target samples 8 from capture molecules are in equilibrium. The linker is then activated (e.g. by light) to strengthen the bindings between target samples 8 and capture molecules 7. Subsequently, the non-bound target samples 8 as well as the unused linkers 24 are washed away. Due to the strengthened bindings between target samples 8 and capture molecules 7 caused by the linkers 24, inadvertent washing away of target samples 8 bound to capture molecules 7 is prevented or at least greatly reduced. Thus, the signal at the detection location can be further enhanced. An example for such process using photo-activated linkers is described in detail in "Capture Compound Mass Spectrometry: A Technology for the Investigation of Small Molecule Protein Interactions", ASSAY and Drug Development Technologies, Volume 5, Number 3, 2007.

Figure 18:
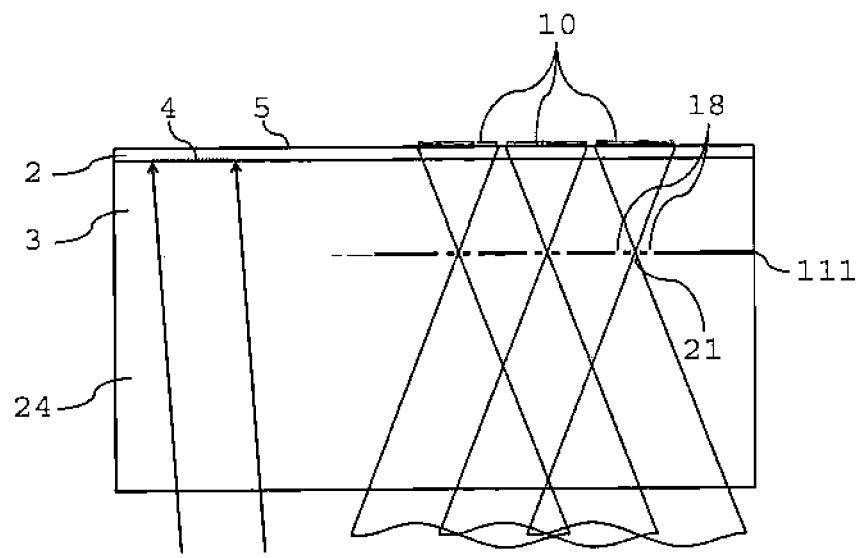
FIG. 18 shows a sectional view of a further embodiment of the device in which the device comprises an additional carrier substrate.

FIG. 18 shows a sectional view of a device which is principally shown in FIG. 1 but which in accordance with a further embodiment has a layer structure to be used for example in highly integrated systems (i.e. up to about $4 \times 10^6$ measurement zones per cm$^2$). In the shown example, the measurement zone 10 has an area of a size of about 25 µm$^2$. This size allows for arranging a multiplicity of measurement zones 10 on the outer surface 5 of the planar waveguide 2 in order to carry out a multiplicity of measurements using a single device. A measurement zone 10 of reduced size is achieved for example by virtually "cutting out" said area of reduced size of 25 µm$^2$ from a larger measurement zone. However, keeping the distance between the predetermined lines in such reduced size measurement zone 10 unchanged would result in that the cone formed by the light scattered at the target samples bound to the binding sites in the reduced size measurement zone 10 would have an aperture angle which is substantially smaller than that of the larger size measurement zone. The smaller aperture angle of the cone of light would result in that the same optical detection unit (comparable to FIG. 2) which has been used for measuring the larger measurement zone and which has a given aperture angle will measure not only light at the detection location but also some incoherent background light. This worsens the signal-to-noise ratio (S/N-ratio). In order to prevent this worsening of the S/N ratio, the distance between the measurement zone 10 and the detection location must be reduced ideally such that the aperture angle of the cone formed by the light scattered by the target samples bound to the binding sites of reduced size measurement zone 10 and interfering at the detection location is identical with the aperture angle of the optical detection unit. For reducing the distance between the reduced size measurement zone 10 and the detection location, the arrangement of the plurality of predetermined lines in the reduced size measurement zone 10 must be determined according to the formula described above with reference to FIG. 3 such that the light scattered by the target samples bound to the binding sites interferes at the new detection location. Since the distance between the reduced size measurement zone 10 and the new detection location is only in the range of ten micrometers (µm) to some hundred micrometers (μm) the thickness of the substrate 3 may become impractically thin. In particular under laboratory conditions it may be disadvantageous to handle devices comprising substrates 3 having a thickness in the range of ten to some hundred micrometers (μm). In order to improve the handling of such device, the device according to this embodiment has the following layer structure (from the lower side to the upper side): an additional carrier substrate 24, a layer 111 of non-transparent material, the substrate 3 and the planar waveguide 2. The additional carrier substrate 24 is made of a transparent material (e.g. glass, plastic) and has a thickness rendering the device suitable to handle (e.g. up to 3 mm). The layer 111 of non-transparent material is formed on top of the additional carrier substrate 24. The layer 111 of non-transparent material is for example a black chromium layer in which the apertures 21, 18 are lithographically formed. The substrate 3 is of a transparent material and has a thickness which corresponds to the distance between reduced size measurement zone 10 and detection location. The planar waveguide 2 and the measurement zones 10 are in principle similar as described further above. Each measurement zone 10 may comprise more than one plurality of predetermined lines, as will be discussed in connection with FIG. 19 below.

Figure 19:
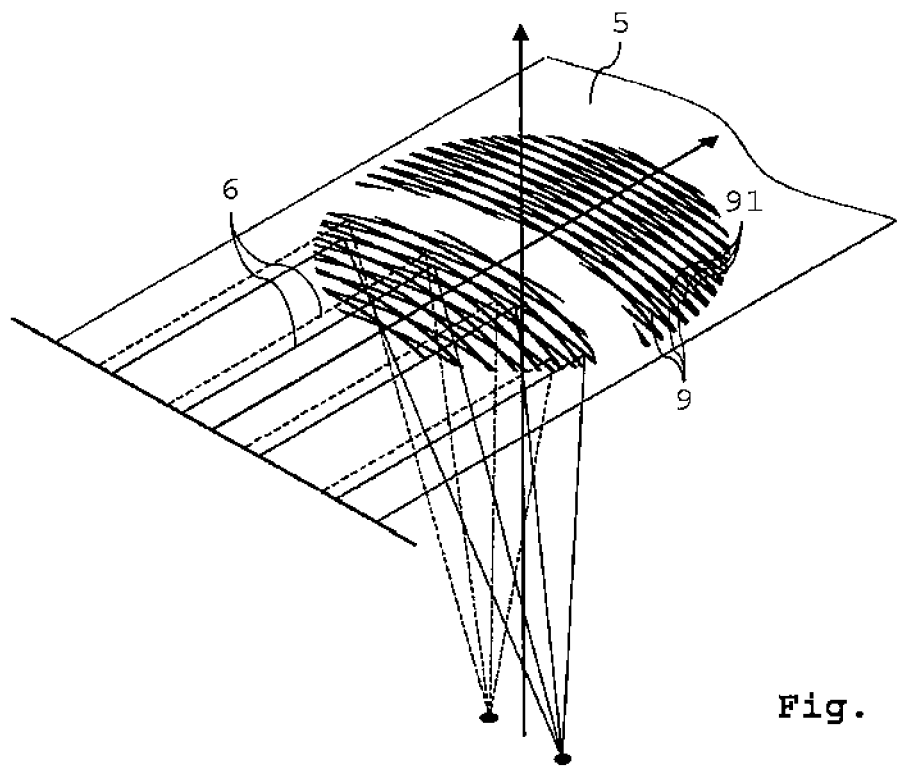
FIG. 19 shows an illustration of different optical paths for the light of the evanescent field scattered at two different pluralities of predetermined lines arranged in a single measurement zone.
Figure 20:
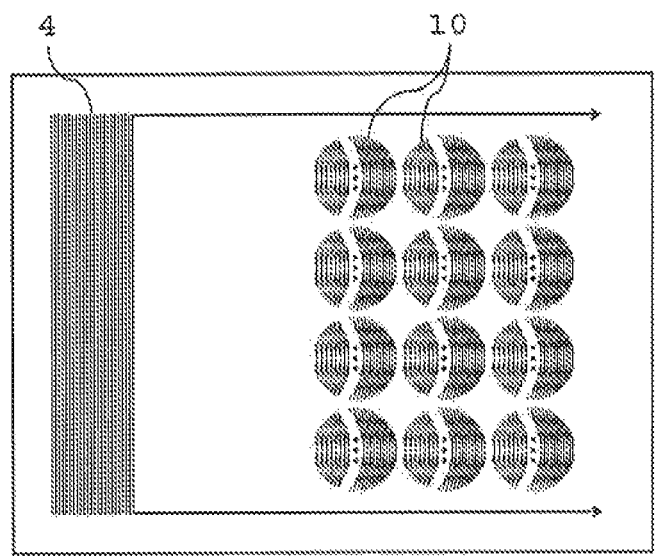
FIG. 20 shows a top view of the device of FIG. 18 having twelve measurement zones arranged thereon, with three pluralities of predetermined lines being arranged in each measurement zone.

The illustration of optical paths in FIG. 19 is similar to FIG. 3. However, two different pluralities of predetermined lines 9, 91 are arranged in a single measurement zone, and in each such zone the light is scattered to different spatially separated detection locations (foci) by the target samples bound to the different pluralities of predetermined lines 9, 91. The light of the evanescent field 6 propagating along the outer surface 5 is scattered at the target samples bound to the binding sites along the first plurality of predetermined lines 9 such as to interfere at the right hand side focus (bold lines) and at the target samples bound to the binding sites along the second plurality of predetermined lines 91 such as to interfere at the left hand side focus (dashed lines). This principle applies for each plurality of predetermined lines 9, 91 in relation to the respective detection location, so that additional pluralities of predetermined lines can be arranged within such measurement zone (for example three as shown in FIG. 20). A target sample which is capable of binding to binding sites arranged at both predetermined lines 9, 91 (FIG. 19) can form cooperative bindings via multiple bond interaction at the intersection of lines 9, 91. Such a multiple bond interaction is of a high strength. Both bindings can be formed simultaneously or sequentially within short periods of time (instantaneously). Such multiple bond interactions are optically detected at two separate detection locations which provide correlated signals at both detection locations.

FIG. 20 shows a top view of the device of FIG. 18 with twelve measurement zones 10 arranged at the outer surface of the planar waveguide. In each measurement zone 10, three pluralities of predetermined lines are provided, and the target samples bound to the binding sites along these three pluralities of predetermined lines scatter the light coupled into the planar waveguide via the optical coupler 4 to three spatially separated individual detection locations. The arrangement of three pluralities is of advantage as process cascades are detectable. Such a process cascade exists for example, when a target sample is split up in separate products at the first type of capture molecule arranged so as to provide a signal at the first detection location. A first product of this reaction does then bind to the second type of capture molecules so as to provide a signal at the second detection location. A second product of the reaction binds to the third type of capture molecule so as to provide a signal at the third detection location.

Figure 21:
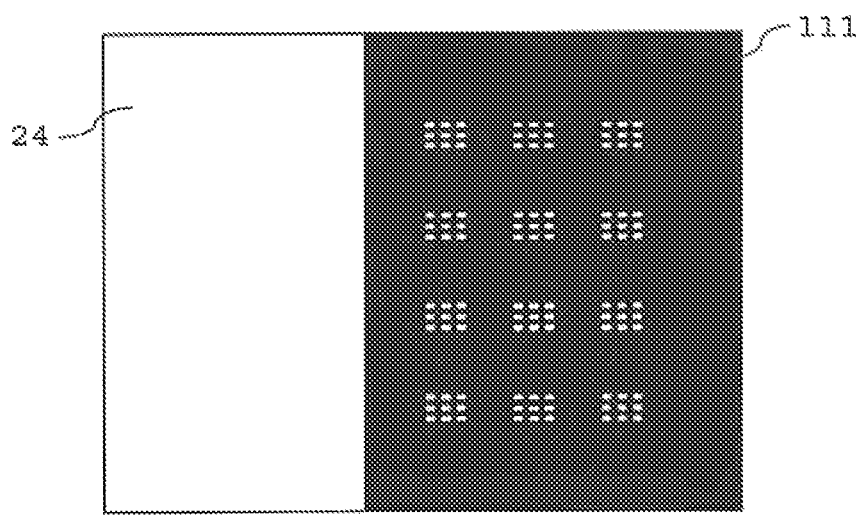
FIG. 21 shows a bottom view of the device of FIG. 18 with apertures in a non-transparent layer formed on top of the additional carrier substrate.

FIG. 21 shows a bottom view of the device of FIG. 20. From below, through the transparent additional carrier substrate 24, the layer 111 of the non-transparent material arranged on top of the additional carrier substrate 24 can be seen. Groups of nine apertures are formed in the layer of non-transparent material 111. Structurally, the layer of non-transparent material 111 comprises several apertures having a shape to mask out any light other than the scattered light needed for the measurement at the respective detection location. For optimal suppression of the diffuse non-coherent background light at the detection location, the diameter of a round aperture is chosen to be larger than the diameter $d_0$ of the focal spot produced by the scattered light interfering at the detection location. In principle, the size is given by Abbe's formula for the calculation of the theoretically possible resolution of the microscope:

$$d_0 = \lambda/2n_s \sin \alpha = \lambda f/n_s D$$

wherein $\lambda$ is the vacuum wavelength of the coherent light propagating in the planar waveguide, $\alpha$ is half the opening angle of the measurement zone, $n_s$ is the refractive index of the substrate 3, f is the focal length of the measurement zone, and D is the diameter of the measurement zone.

Further apertures are formed in the non-transparent layers 111 in front of and behind the apertures 21 (see FIG. 18) to determine an average background signal. The shape of the apertures can be chosen so as to correspond to the shape of the focal spot formed by the light which interferes at the detection location. It may be advantageous to provide an elongated aperture 21 (extending in the direction of propagation of the evanescent field) in order to avoid cutting off the light to be detected in the detection location with the edge of the aperture, for example in case of changes in the location of the focal spot caused by changes in the refractive index of the sample applied to the outer surface of the planar waveguide or caused by small changes in the thickness of the planar waveguide.

While the embodiments of the invention have been described with the aid of the drawings, various modifications and changes to the described embodiments are possible without departing from the general teaching underlying the invention. Therefore, the invention is not to be understood as being limited to the described embodiments, but rather the scope of protection is defined by the claims.

The invention claimed is:

1. A method for detection of binding affinities of target samples to binding sites, the method comprising the steps of:
    providing a device comprising a planar waveguide arranged on a substrate and an optical coupler,
    coupling coherent light of a predetermined wavelength into the planar waveguide such that the coherent light propagates along the planar waveguide with an evanescent field of the coherent light propagating along an outer surface of the planar waveguide,
    attaching the target samples to the binding sites arranged along a plurality of predetermined lines on the outer surface of the planar waveguide,
    detecting, at a predetermined detection location, light of the evanescent field scattered by the target samples bound to the binding sites arranged along the predetermined lines, the light scattered by the target samples bound to the binding sites having, at the predetermined detection location, a difference in optical path length which is an integer multiple of the predetermined wavelength of the light, and from the light detected at the predetermined detection location, determining the binding affinities of the target samples to the binding sites.

2. A method according to claim 1, wherein the predetermined lines with the target samples attached thereto are arranged such that the coherent light scattered by the target samples bound to the binding sites interferes at the predetermined detection location with a difference in optical path length which is an integer multiple of the predetermined wavelength of the coherent light, so that a maximum of light scattered by the target samples bound to the binding sites is located at the predetermined detection location, and wherein binding of the target samples to the binding sites is determined when the said maximum of light scattered by the target samples bound to the binding sites is detected at the predetermined detection location.

3. A method according to claim 1, wherein the distance between adjacent predetermined lines decreases in the direction of propagation of the light of the evanescent field.

4. A method according to claim 1, wherein the plurality of predetermined lines along which the binding sites are arranged comprises curved lines, the curvature of the lines being such that light of the evanescent field scattered by the target samples bound to the binding sites interferes at a predetermined detection point as detection location.

5. A method according to according to claim 1, wherein the plurality of predetermined lines are arranged on the outer surface of the planar waveguide in a manner such that their locations are geometrically defined by the equation $$x_j = \frac{\lambda N(A_0 + j) - \sqrt{n_s^2(N^2 - n_s^2)(y_j^2 + f^2) + (n_s\lambda)^2(A_0 + j)^2}}{N^2 - n_s^2}$$

wherein:
$\lambda$ is the vacuum wavelength of the propagating light,
N is the effective refractive index of the guided mode in the planar waveguide; N depends on the thickness and the refractive index of the planar waveguide, the refractive index of the substrate, the refractive index of a medium on the outer surface of the planar waveguide and the polarization of the guided mode,
$n_s$ is the refractive index of the substrate,
f is the thickness of the substrate,
$A_0$ is an integer which is chosen to be close to the product of the refractive index $n_s$ and the thickness f of the substrate divided by the wavelength $\lambda$, and
j is a running integer that indicates the index of the respective line.

6. A method according to claim 1, wherein the binding sites comprise capture molecules attached to the surface of the planar waveguide along the predetermined lines only, the capture molecules being capable of binding the target samples.

7. A method according to claim 1, wherein the binding sites comprise capture molecules capable of binding the target samples, the capture molecules capable of binding the target samples being arranged along the predetermined lines by dispensing capture molecules capable of binding the target samples onto the outer surface of the planar waveguide and by deactivating those capture molecules which are not arranged along the predetermined lines.

8. A method according to claim 1, wherein the planar waveguide has a refractive index ($n_w$) which is substantially higher than the refractive index ($n_s$) of the substrate and which is also substantially higher than the refractive index ($n_{med}$) of the medium on the outer surface of the planar waveguide, such that for a predetermined wavelength of the light the evanescent field has a penetration depth in the range of 50 nm to 200 nm.

9. A method according to claim 1, wherein the device comprises a further optical coupler for coupling out the light that has propagated through the planar waveguide, wherein both the optical coupler for coupling the light into the planar waveguide as well as the further optical coupler for coupling out the light that has propagated through the planar waveguide comprise an optical grating for coherently coupling light into and out of the planar waveguide.

10. A method according to claim 1, wherein the planar waveguide has a first end section and a second end section which are arranged at opposite ends of the planar waveguide with respect to the direction of propagation of the light through the planar waveguide, the first end section and the second end section each comprising a material which is absorptive at the wavelength of the light propagating through the planar waveguide.

11. A method according to claim 1, wherein a plurality of measurement zones are arranged on the outer surface of the planar waveguide, wherein in each measurement zone the binding sites are arranged along the plurality of predetermined lines.

12. A method according to claim 11, wherein the plurality of measurement zones comprises measurement zones of different sizes.

13. A method according to claim 11, wherein each measurement zone has an area larger than 25 $\mu m^2$, and wherein the plurality of predetermined lines has a distance between adjacent predetermined lines less than 1.5 $\mu m$.

14. A method according to claim 11, wherein the binding sites are arranged along at least two pluralities of predetermined lines in a single measurement zone, each of the two pluralities of predetermined lines being arranged such that the light scattered by the target samples bound to the binding sites arranged along the respective plurality of predetermined lines interferes with a difference in optical path length which is an integer multiple of the predetermined wavelength of the light at an individual detection location for each plurality of predetermined lines with the individual detection locations being spatially separated from each other.

15. A method according to claim 11, wherein the device further comprises a diaphragm having an aperture which is arranged such that light at the detection location is allowed to pass through the aperture while light at a location different from the detection location is blocked by the diaphragm.

16. A method according to claim 15, wherein the diaphragm further comprises at least one further aperture which is arranged adjacent to the aperture when viewed in the direction of propagation of the light through the planar waveguide.

17. A method according to claim 11, wherein each measurement zone has an area larger than 25 $\mu m^2$, and wherein the plurality of predetermined lines has a distance between adjacent predetermined lines less than 1.0 $\mu m$.

18. A method according to claim 1, wherein the device further comprises a light source for emitting the coherent light of the predetermined wavelength, the light source being arranged such that the coherent light is coupled into the planar waveguide via the optical coupler.

19. A method according to claim 1, wherein the device further comprises an optical imaging unit, the optical imaging unit being focused such as to produce an image of the detection location to an observation location.

20. A method according to claim 1, wherein the device further comprises a photo-detector for measuring the intensity of the light at the detection location.

* * * * *